(12) United States Patent
Urano et al.

(10) Patent No.: US 9,678,021 B2
(45) Date of Patent: Jun. 13, 2017

(54) METHOD AND APPARATUS FOR INSPECTING DEFECTS

(71) Applicant: HITACHI HIGH-TECHNOLOGIES CORPORATION, Minato-ku, Tokyo (JP)

(72) Inventors: Yuta Urano, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 46 days.

(21) Appl. No.: 14/821,075

(22) Filed: Aug. 7, 2015

(65) Prior Publication Data
US 2016/0041092 A1 Feb. 11, 2016

(30) Foreign Application Priority Data

Aug. 8, 2014 (JP) .................. 2014-162012

(51) Int. Cl.
*G01N 21/00* (2006.01)
*G01N 21/956* (2006.01)
*G01N 21/95* (2006.01)

(52) U.S. Cl.
CPC ... *G01N 21/95623* (2013.01); *G01N 21/9501* (2013.01); *G01N 2021/9513* (2013.01); *G01N 2201/0638* (2013.01)

(58) Field of Classification Search
USPC ............ 356/237.1–237.6, 239.1–239.8
See application file for complete search history.

(56) References Cited

U.S. PATENT DOCUMENTS

| | | | |
|---|---|---|---|
| 5,442,189 A | 8/1995 | Hagiwara | |
| 7,365,834 B2 | 4/2008 | Lewis et al. | |
| 7,639,350 B2 * | 12/2009 | Noguchi | B82Y 15/00 356/237.2 |

FOREIGN PATENT DOCUMENTS

| | | |
|---|---|---|
| JP | 6-109647 A | 4/1994 |
| JP | 4838122 B2 | 12/2011 |

* cited by examiner

*Primary Examiner* — Tri T Ton
(74) *Attorney, Agent, or Firm* — Miles & Stockbridge P.C.

(57) ABSTRACT

In optical dark field defect inspection, the present invention provides including: condensing laser emitted from a light source in a line shape; reflecting the laser, with a mirror; irradiating the reflected laser via an objective lens to a sample placed on a table from a vertical direction; condensing reflected scattered light from the sample with the objective lens; shielding diffraction light occurred from a periodical pattern formed on the sample, in the reflected scattered light from the sample and scattered light occurred from the mirror, with a spatial filter; receiving the reflected scattered light from the sample, not shielded with the spatial filter, with an imaging lens, and forming an image of the reflected scattered light; detecting the image of the reflected scattered light; and processing a detection signal obtained by detecting the image of the reflected scattered light and detecting a defect on the sample.

10 Claims, 10 Drawing Sheets

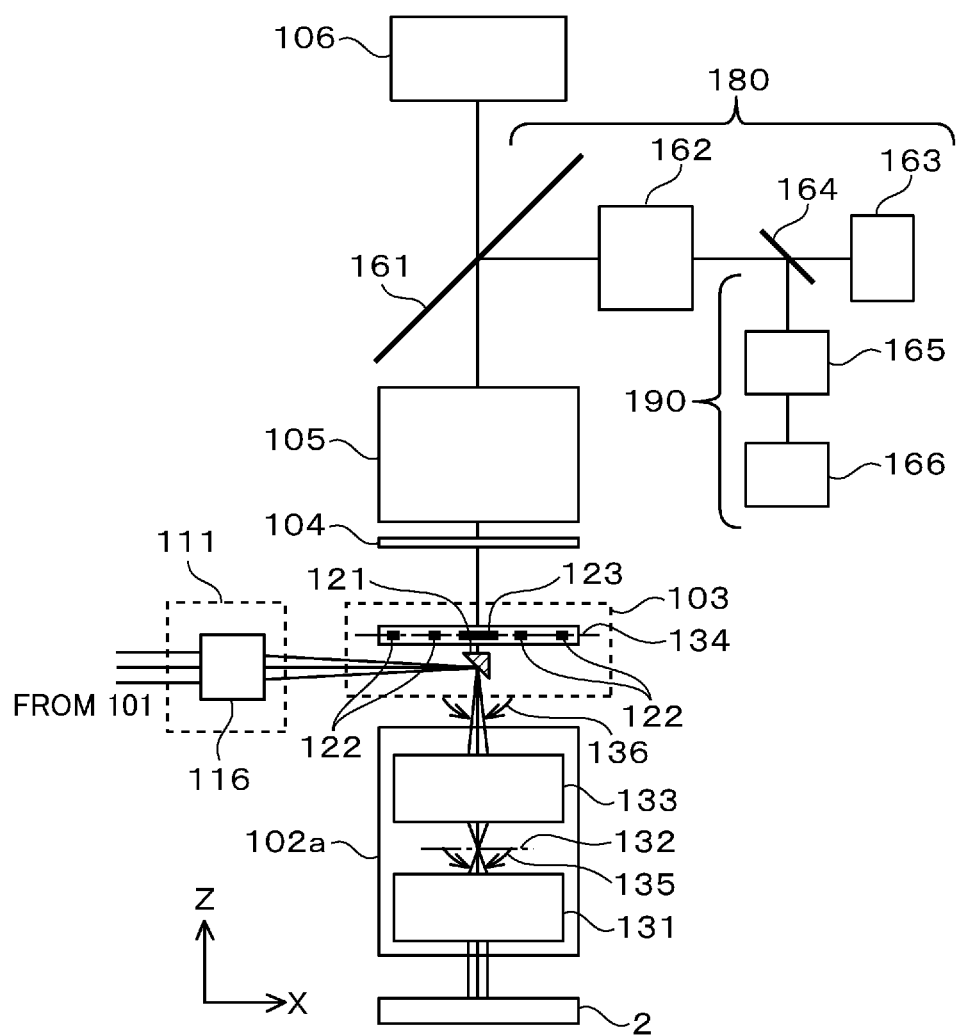
F I G. 4 B

F I G. 1 1 A
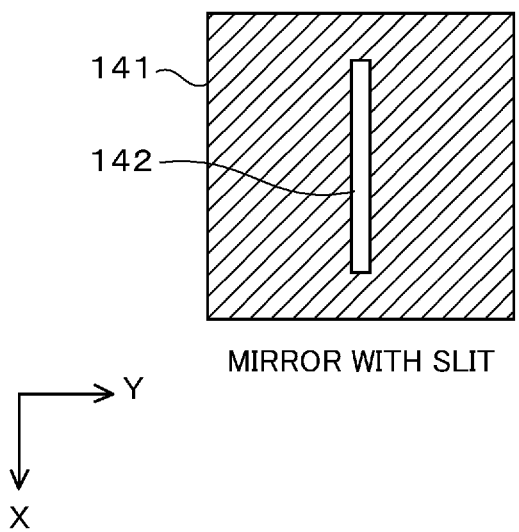
MIRROR WITH SLIT
F I G. 1 1 B
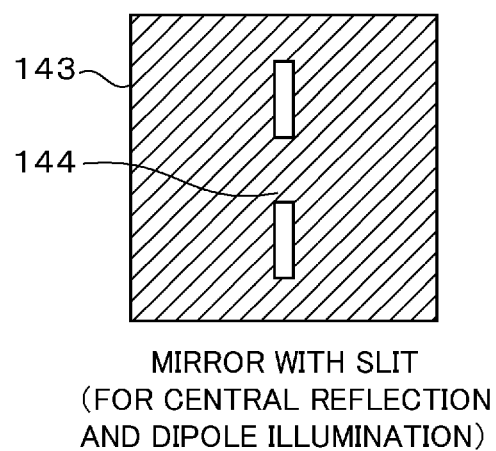
MIRROR WITH SLIT
(FOR CENTRAL REFLECTION
AND DIPOLE ILLUMINATION)

METHOD AND APPARATUS FOR INSPECTING DEFECTS

BACKGROUND

The present invention relates to a defect inspecting apparatus and a defect inspecting method for inspection of a defect occurrence situation in manufacturing processes for pattern formation on a substrate to manufacture an object, such as a semiconductor manufacturing process, a liquid crystal display device manufacturing process, and a printed circuit board manufacturing process, in which a defect when detected is analyzed and countermeasures are taken.

As a background art of the technical field, Japanese Patent No. 4838122 is known. This publication discloses "An optical apparatus comprising: a second optical instrument to focus a radiation beam at a second incidence angle in a vertical or approximately vertical direction with respect to an illuminated region on a sample surface on a second focused optical beam, wherein the second incidence angle being different from the first incidence angle; an elongated reflecting surface to reflect radiation beam in the beam focused with the second optical instrument with respect to the illuminated region on the sample surface; a first detector array; and a light concentrating optical instrument to condense a radiation beam, occurred from the first and/or second focused beam and scattered or reflected from a first line and/or illuminated region on the sample surface, and focus a radiation beam condensed from a part of the line and/or the illuminated region on a corresponding detector in the first array, wherein arrival of a radiation beam in the beam focused with the second optical instrument and mirror-reflected with the illuminated region on the sample surface at the first detector array being prevented with the elongated reflecting surface" (claim 1 of claims).

Further, FIG. 12 of the Japanese Patent No. 4838122 illustrates a configuration where a narrow mirror 250 is provided above an objective lens 222. A beam emitted from a light source is reflected with the narrow mirror 250, then is irradiated via the objective lens 222 to the sample. The reflection light from the sample is detected with a detection systems provided in an upper position and an oblique position. The detection system provided in the upper position performs detection while selecting a wavelength with a filter 272 to transmit light having a wavelength $\lambda 1$ of the reflection light not shielded with the narrow mirror 250 in the reflection light from the sample, but shielding light having a wavelength $\lambda 2$.

As another background art of the present technical field, Japanese Published Unexamined Patent Application No. Hei 6-109647 is known. This publication discloses "A defect inspecting apparatus having: a first lens to form an optical Fourier-transformed image of an inspection pattern; and a second lens to perform inverse Fourier transformation on the Fourier-transformed image, wherein an image of a defect in the inspection pattern is projected with the second lens, comprising: illumination means for illuminating a dot or line shaped illuminated region on the inspection pattern; optical filter means for eliminating a component corresponding to the Fourier-transformed image when the defect does not exist in the inspection pattern from the optical Fourier-transformed image of the inspection pattern; photodetection means for photoelectric converting the image of the defect of the inspection pattern projected with the second lens; and relative scan means for relative displacement of the inspection pattern and the illumination means." (claim 1 of claims).

FIG. 2 of the Japanese Published Unexamined Patent Application No. Hei 6-109647 illustrates a configuration where light emitted from a light source is reflected with a reflecting mirror 9 and irradiated as a slit-shaped light beam via an objective lens 10 to the sample. In the light refracted on the sample surface and transmitted through the objective lens 10, light not shielded with the reflecting mirror is detected via a space filter provided on the Fourier transformation plane of the objective lens 10.

SUMMARY

Japanese Patent No. 4838122 and Japanese Published Unexamined Patent Application No. Hei 6-109647 disclose a configuration in optical dark-field type defect inspection to perform TTL (Through The Lens) illumination, incident from a normal direction of an inspection object surface via an objective lens of a detection optical system. The light emitted from a light source is reflected with a mirror provided above the objective lens and irradiated to an inspection object sample. Then specular reflection light of reflected scattered light from the inspection object sample is shielded with a mirror, and light not shielded with a filter in the other reflected scattered light is detected.

In the optical dark-field type defect inspection to perform TTL illumination, in some cases, in a Fourier transformation plane of the objective lens, the scattered light component from a defect is distributed in the vicinity of specular reflection light reflected in the normal direction from the inspection object sample. Accordingly, it is desirable that in the reflection light reflected in a direction in the vicinity of a normal line from the inspection object sample incident on the objective lens, the quantity of the scattered light shielded with the mirror provided above the objective lens other than the specular reflection light is reduced, i.e., the scattered light is detected as much as possible in the vicinity of the specular reflection light, for high sensitivity defect detection.

However, when the specular reflection light is shielded with the mirror, as illumination light or a part of a beam of the specular reflection light from the inspection object surface is incident on the mirror provided above the objective lens, scattered light occurs. When the scattered light occurred from the mirror is detected without any processing, the scattered light component becomes noise. Then it is difficult to raise the sensitivity of defect detecting. There is no consideration of the influence of the scattered light occurred from the mirror to shield the specular reflection light in either of Japanese Patent No. 4838122 and Japanese Published Unexamined Patent Application No. Hei 6-109647.

To detect a defect from which scattered light is distributed in the vicinity of specular reflection light (for example, a bridge defect in a line and space pattern) with high sensitivity, there is a problem that the scattered light occurred from this mirror becomes noise, which is a bottleneck of improvement in the inspection sensitivity.

The present invention has been made to solve the problem in the conventional art, and provides a defect inspecting apparatus and a defect inspecting method to enable high sensitivity defect detection in optical dark-field type defect inspection with TTL illumination, by detecting reflection light (scattered light) in the vicinity of specular reflection light from an inspection object sample as much as possible while avoiding detection of scattered light component as noise as much as possible.

To solve the above problem, the present invention provides a defect inspecting apparatus including: a table unit placing a sample, capable of moving within a plane; a light source that emits laser; an optical path branching unit that branches an optical path of the laser emitted from the light source; an oblique illumination unit that condenses the laser, proceeded in one of optical paths branched with the optical path branching unit, into a line shape, and irradiates the laser to the sample placed on the table unit from an oblique direction; a condensing unit that condenses the laser, proceeded in another one of optical paths branched with the optical path branching unit, into a line shape; a mirror unit that reflects the laser, condensed in a line shape with the condensing unit, to deflect the optical path of the laser; an objective lens unit that receives the laser, with the optical path deflected with the mirror unit, then irradiates the laser to the sample placed on the table unit from a vertical direction, and condenses reflected scattered light from the sample irradiated with the laser; a spatial filter unit that shields diffraction light, occurred from a periodical pattern formed on the sample, in the reflected scattered light from the sample, condensed with the objective lens unit, and shields the scattered light occurred from the mirror unit; an imaging lens unit that receives the reflected scattered light from the sample, not shielded with the spatial filter, and forms an image of the reflected scattered light; a detection unit that detects the image of the reflected scattered light formed with the imaging lens unit; and a signal processing unit that processes a detection signal obtained by detecting the image of the reflected scattered light with the detection unit, to detect a defect on the sample.

Further, to solve the above problem, the present invention provides a defect inspecting method including: condensing laser emitted from a light source in a line shape; reflecting the laser, condensed in the line shape, with a mirror; irradiating the reflected laser via an objective lens to a sample placed on a table from a vertical direction; condensing reflected scattered light from the sample, irradiated with the laser from the vertical direction, with the objective lens; shielding diffraction light occurred from a periodical pattern formed on the sample, in the reflected scattered light from the sample, condensed with the objective lens, and scattered light occurred from the mirror, with a spatial filter; receiving the reflected scattered light from the sample, not shielded with the spatial filter, with an imaging lens, and forming an image of the reflected scattered light; detecting the formed image of the reflected scattered light with a detector; and processing a detection signal obtained by detecting the image of the reflected scattered light with the detector and detecting a defect on the sample.

According to the present invention, it is possible to perform inspection on a defect to emit scattered light in a direction in the vicinity of the normal line of the inspection object surface with high sensitivity. Further, it is possible to detect a bridge defect in a line and space pattern with high sensitivity.

These features and advantages of the invention will be apparent from the following more particular description of preferred embodiments of the invention, as illustrated in the accompanying drawings.

BRIEF DESCRIPTION OF THE DRAWINGS

FIG. 4B is a block diagram showing a schematic configuration of the vertical detection unit of the defect inspecting apparatus according to the embodiment of the present invention viewed from a side direction;

FIG. 11A is a front diagram of the mirror with a single slit in the defect inspecting apparatus according to the second modification of the present invention; and FIG. 11B is a front diagram of the mirror with two separate slits in the defect inspecting apparatus according to the second modification of the present invention.

DESCRIPTION OF THE PREFERRED EMBODIMENTS

In an embodiment of the present invention, an example of a defect inspecting apparatus and a defect inspecting method for inspection of a defect occurrence situation in manufacturing processes for pattern formation on a substrate to manufacture an object, such as a semiconductor manufacturing process, a liquid crystal display device manufacturing process, and a printed circuit board manufacturing process, in which a defect when detected is analyzed and countermeasures are taken, will be described.

Embodiment

Figure 1:
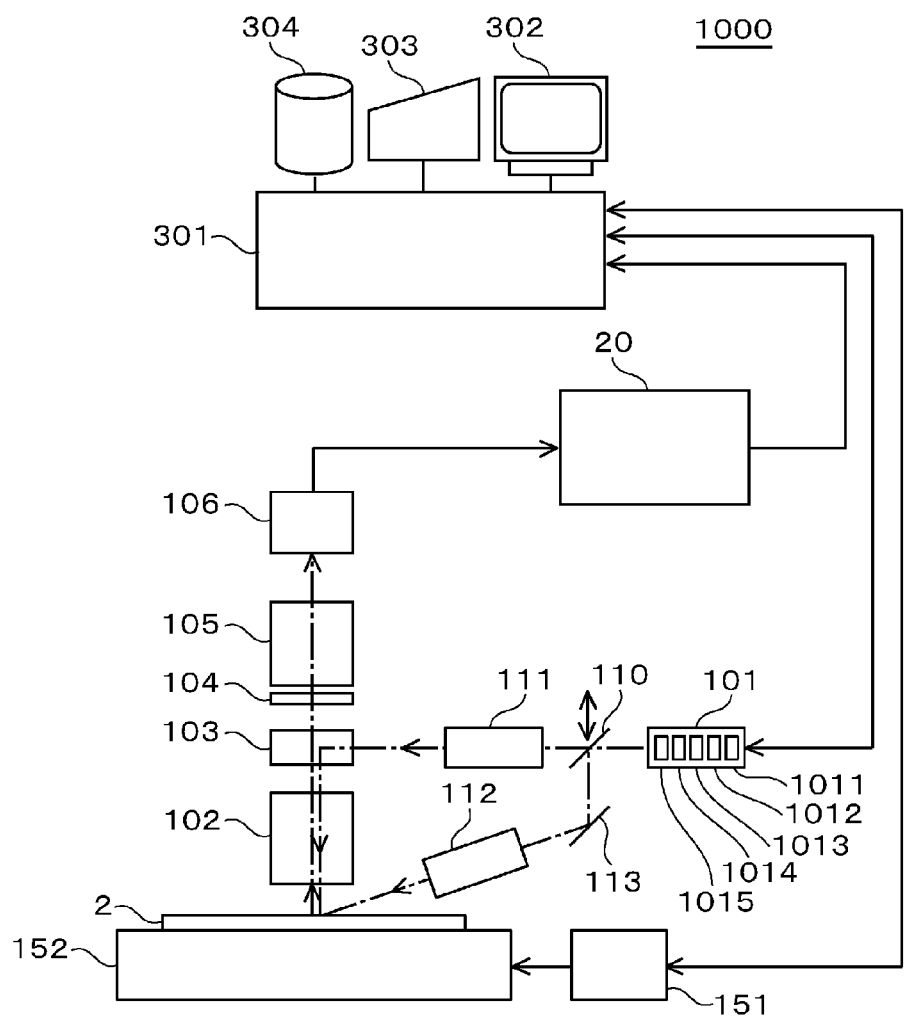
FIG. 1 is a block diagram showing a schematic configuration of a defect inspecting apparatus according to an embodiment of the present invention.

FIG. 1 shows an example of the configuration of a defect inspecting apparatus 1000 according to the present embodiment. The defect inspecting apparatus 1000 shown in FIG. 1 has a light source unit 101, a TTL illumination unit 111, an oblique illumination unit 112, an objective lens 102, an objective pupil optical unit 103, an imaging lens 105, a detector 106, a processor 20, an overall control unit 301, a display unit 302, an arithmetic unit 303, a storage unit 304, a stage driving unit 151, and an X-Y-Z-θ stage 152 (hereinbelow, "stage 152").

The outline of the operation of the defect inspecting apparatus 1000 according to the present embodiment shown in FIG. 1 will be described.

Illumination light emitted from the light source unit 101 is reflected with a mirror 110, and its optical path is deflected to the mirror 113 side. The light is reflected with the mirror 113, then enters the oblique illumination unit 112. The light is condensed in a line shape, and the line-shaped illumination light is irradiated to an inspection object substrate 2 from an oblique direction. Further, when the mirror 110 is moved by unshown means to a position out of the optical path of the illumination light emitted from the light source unit 101, the illumination light emitted from the light source unit 101 enters the TTL illumination unit 111. The illumination light entered the TTL illumination unit 111 is condensed in a line shape, and enters the objective pupil optical unit 103, in which the optical path is deflected to the objective lens 102 side. Then the illumination light condensed in a line shape passes through the objective lens 102 and irradiates the inspection object substrate 2 from a normal direction.

The reflection light, diffraction light, and scattered light (hereinbelow, these lights will be generally referred to as "reflection light") which are emitted from the inspection object substrate 2 irradiated with the illumination light from the oblique direction with the oblique illumination unit 112, or from the inspection object substrate 2 irradiated with the illumination light condensed in a line shape from the normal direction with the objective lens 102 via the TTL illumination unit 111, enter the objective lens 102 and condensed there. Then image is formed on a detection surface 106' of the detector 106 (see FIG. 6A) via the objective pupil optical unit 103, a polarizer 104 and the imaging lens 105, and the image is detected by the detector 106 and converted into an electric signal. Note that the polarizer 104 may be arranged between the imaging lens 105 and the detector 106, and immediately in front of the detector 106.

The electric signal obtained with the detector 106 is inputted into the processor 20. In the processor 20, the input signal is compared with a previously-set threshold value, and a defect is detected. As a detected result, defect signal level information (luminosity value of defect signal) and defect signal detection position information obtained from the stage 152 are stored via the overall control unit 301 into the storage unit 304, and displayed on the display unit 302. The inspection object substrate 2 is scanned with the stage 152 driven with the stage driving unit 151, and the entire surface is inspected.

The light source unit 101 has a laser light source 1011, an attenuator 1012, an ND filter 1013, a wavelength plate 1014, and a beam expander 1015. In the light source unit 101, the output of the laser emitted from the laser light source 1011 is adjusted with the attenuator 1012. The light quantity is adjusted with the ND filter 1013. The polarized status is adjusted with the wavelength plate 1014. The beam diameter and the shape of the laser are adjusted with the beam expander 1015. Then the laser is emitted as adjusted illumination light.

The optical path of the illumination light emitted from the light source unit 101 is branched with the mirror 110, and guided to the TTL illumination unit 111 or the oblique illumination unit 112. That is, when the mirror 110 is driven with the unshown driving means and positioned out of the optical path of the illumination light emitted from the light source unit 101, the illumination light emitted from the light source unit 101 enters the TTL illumination unit 111. On the other hand, when the mirror 110 is driven with the unshown driving means and positioned on the optical path of the illumination light emitted from the light source unit 101, the illumination light emitted from the light source unit 101 is reflected with the mirror 110 and its optical path is deflected to the mirror 113 side. Then the light is reflected with the mirror 113, and enters the oblique illumination unit 112. The illumination light, which is entered the TTL illumination unit 111 or the oblique illumination unit 112, is transformed into a light beam long in one direction, and emitted from the TTL illumination unit 111 or the oblique illumination unit 112.

As the laser light source 1011, a short wavelength, high-output, high-luminance and highly-stable light source is appropriately used. For example, a light source using YAG laser of the third, fourth or fifth harmonic wave is used.

FIG. 1 shows only one detector configured with the objective lens 102, the objective pupil optical unit 103, the imaging lens 105, and the detector 106 as a constituent element of the defect inspecting apparatus 1000. The detector may be provided in plural positions where the respective objective lenses do not mechanically interfere with each other. In this case, the processor 20 processes signals detected with the plural detecting units and determines a defect.

Figure 2A:
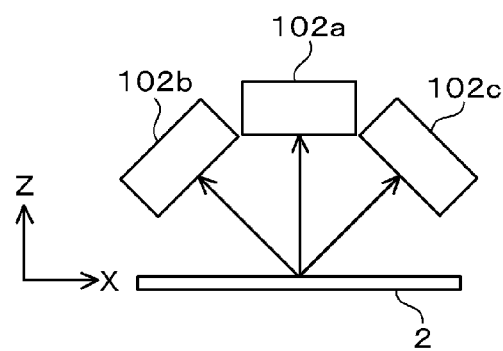
FIG. 2A is a block diagram showing positional relation among respective objective lenses of plural detection units of the defect inspecting apparatus according to the embodiment of the present invention.
Figure 2B:
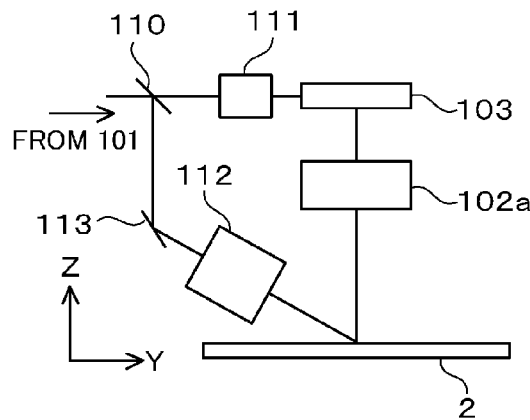
FIG. 2B is a block diagram showing schematic positional relation between an oblique illumination unit and a TTL illumination unit of the defect inspecting apparatus according to the embodiment of the present invention.

FIG. 2A shows an example of positional relation among the respective objective lenses 102a, 102b and 102c of the plural detecting unit, as a configuration having plural detecting unit. A detecting unit having the objective lens 102a will be referred to as a "vertical detection unit 170a"; a detecting unit having the objective lens 102b, a "left oblique detection unit 170b"; and a detecting unit having the objective lens 102c, a "right oblique detection unit 170c". FIG. 2B shows a configuration of the objective lens 102a corresponding to the vertical detection unit 170a, the TTL illumination unit 111, the objective pupil optical unit 103, and the oblique illumination unit 112. This configuration corresponds to the configuration of the defect inspecting apparatus 1000 including the objective lens 102 shown in FIG. 1.

Figure 2C:
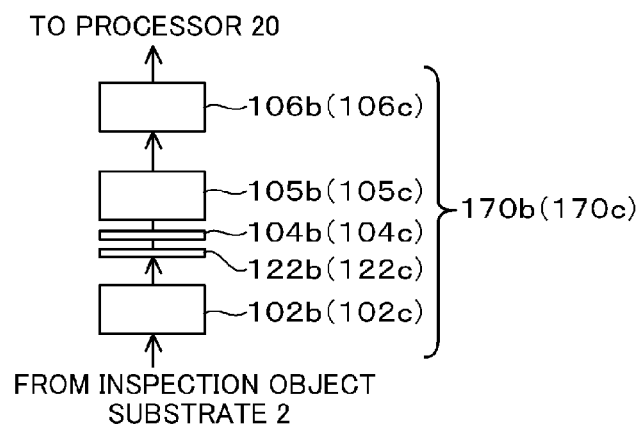
FIG. 2C is a block diagram showing a schematic configuration of the oblique detection unit of the defect inspecting apparatus according to the embodiment of the present invention.

FIG. 2C shows a configuration of the left oblique detection unit 170b and the right oblique detection unit 170c corresponding to the objective lens 102b and the objective lens 102c respectively. Since optical systems corresponding to the objective lens 102b and the objective lens 102c basically have the same configuration, FIG. 2C shows the configuration of one of the optical systems. The left oblique detection unit 170b and the right oblique detection unit 170c have the objective lens 102b (102c), the spatial filter 122b (122c), the polarizer 104b (104c), the imaging lens 105b

(105c), and the detector 106b (106c). The present configuration differs from the configuration of a vertical detection unit 201a in that it lacks a TTL illumination mirror 121 and a mirror scattered light shielding filter 123 of the objective pupil optical unit 103.

In FIGS. 2A and 2B, a plane including the inspection object substrate 2 is an XY plane, and a normal direction of the inspection object substrate 2 is a Z direction. The main scanning direction of the stage 152 is an X-direction, and the subscanning direction, a Y-direction. The objective lenses 102a, 102b and 102c respectively corresponding to the three detecting units have an optical axis in the XZ plane. The objective lens 102a is provided in the Z-direction, and detects light emitted in the Z-direction (the vertical detection unit 170a). The objective lenses 102b and 102c are provided on both sides of the objective lens 102a, and detect light emitted in a direction inclined from the Z-direction (the left oblique detection unit 170b and the right oblique detection unit 170c).

The illumination light emitted from the light source unit 101 is guided to the TTL illumination unit 111 or the oblique illumination unit 112 by input/output to/from the optical path of the illumination light with the mirror 110 for optical path switching driven with unshown driving means.

Further, it may be configured such that the illumination light is guided to both of the TTL illumination unit 111 and the oblique illumination unit 112, by using optical path branching with a beam splitter in place of the mirror 110 for optical path switching. In this case, it is possible to simultaneously irradiate the illumination light from the TTL illumination unit 111 and the oblique illumination unit 112 to the surface of the inspection object substrate 2.

The illumination light, formed through the TTL illumination unit 111 in a shape elongated in one direction, is guided to the objective pupil optical unit 103 provided in a pupil position (objective pupil plane) 134 of the objective lens 102a. Then the optical path is changed to the inspection object substrate 2 side, and is guided via the objective lens 102a to the inspection object substrate 2.

On the other hand, the illumination light, reflected with the mirror 110 and the mirror 113 then entered the oblique illumination unit 112, is emitted from the oblique illumination unit 112, in a light beam shape elongated in one direction, and guided in a YX plane to the inspection object substrate 2 through outside the objective lens 102a.

The illumination light is condensed with the above optical system in a line beam shape elongated in the Y direction and short in the X direction on the surface of the inspection object substrate 2. The view fields of the plural detectors are incorporated together in the condensing position of the illumination light.

Figure 3:
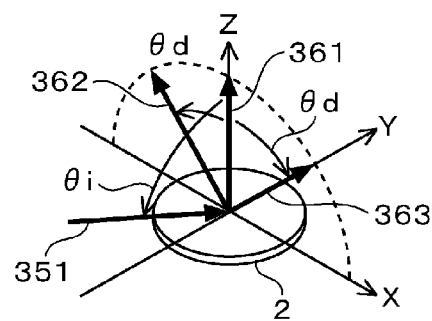
FIG. 3 is a perspective diagram of an inspection object substrate showing relation between an incident direction of oblique illumination to the inspection object substrate and a detection direction of the plural detection units in the embodiment of the present invention.

FIG. 3 shows relation between an incident direction 351 of the oblique illumination and detection directions 361 to 363 of the plural detectors. An incident angle in the incident direction 351 of the oblique illumination is θi, and a detection angle in the detection directions 361 and 363 of the oblique detection unit for detection from a direction inclined from the normal line of the inspection object substrate is θd. Two oblique detection units (left oblique detection unit 210b and right oblique detection unit 210c) are provided in mutually symmetrical directions (±θd) with the YZ plane as a reference.

Figure 4A:
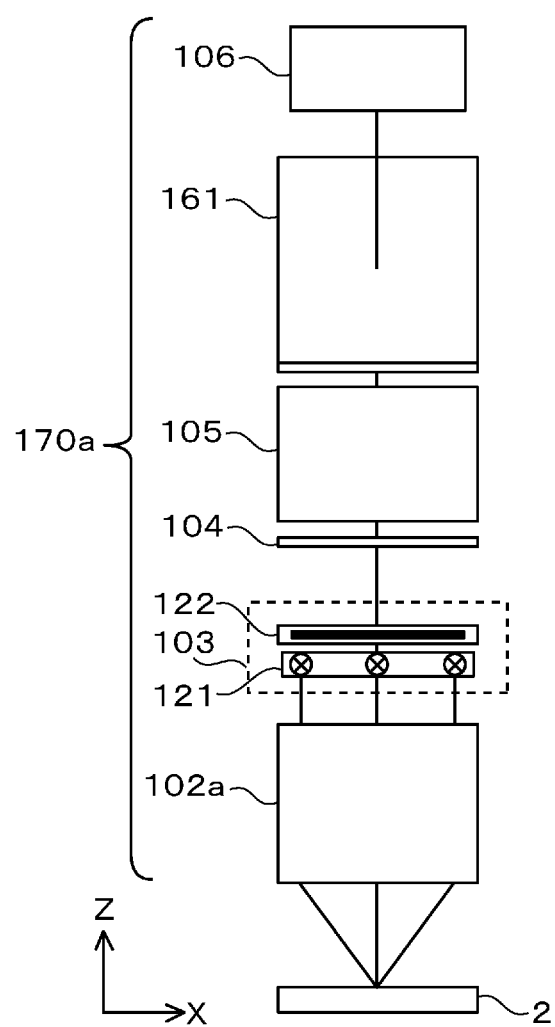
FIG. 4A is a block diagram showing a schematic configuration of a vertical detection unit of the defect inspecting apparatus according to the embodiment of the present invention viewed from a front direction.

FIGS. 4A and 4B show a configuration of the vertical detection unit 170a. FIG. 4A is a cross-sectional diagram in the XZ plane of the vertical detection unit 170a. FIG. 4B is a cross-sectional diagram in the YZ plane of the vertical detection unit 170a.

The TTL illumination unit 111 has a cylindrical lens 116. The objective pupil optical unit 103 has the TTL illumination mirror 121, the spatial filter 122, and the mirror scattered light shielding filter 123. The TTL illumination mirror 121 is a mirror in a shape elongated in the X direction. The TTL illumination mirror 121 is provided in the vicinity of a pupil plane (objective pupil plane) 134 of the objective lens 102a and on a position closer to the objective lens 102a from the objective pupil plane 134. The illumination light incident from the TTL illumination unit 111, formed with the cylindrical lens 116 in a beam shape elongated in one direction, is reflected with the TTL illumination mirror 121 to the objective lens 102a side, and condensed in the Y direction so as to have a shape elongated in the X direction in a position corresponding to the objective pupil plane 134 of the objective lens 102a.

The objective lens 102a is a Fourier transformation lens in which the spatial filter 122 and the mirror scattered light shielding filter 123 (the spatial filter 122 and the mirror scattered light shielding filter 123 may be generally referred to as a "spatial filter") are provided in the objective pupil plane (Fourier transformation plane) 134. The objective lens 102a has a condensing lens 131 and a pupil relay lens 133. The condensing lens 131 forms a first pupil plane 132. The pupil relay lens 133 re-forms it into the objective pupil plane 134. Accordingly, the first pupil plane 132 and the objective pupil plane 134 are optically conjugate. With this configuration having a pupil relay optical system to re-form the first pupil plane 132 to form the objective pupil plane 134 as a second pupil plane, in lens design, the objective pupil plane 134 as a pupil conjugate plane can be formed not inside the lens barrel of the objective lens 102a but outside the objective lens 102a. This simplifies the configuration of the objective lens 102a and attains cost reduction.

Further, as the pupil relay lens 133 is a magnifying image formation optical system, a divergence angle 136 in the objective pupil plane 134 magnify-formed with the pupil relay lens 133 becomes smaller with respect to the divergence angle 135 of the light beam of the specular reflection light from the inspection object substrate 2 in the first pupil plane 132. The ratio between the divergence angle 135 of the light beam of the specular reflection light from the inspection object substrate 2 in the first pupil plane 132 and the divergence angle 136 of the light beam in the objective pupil plane 134 magnify-formed with the pupil relay lens 133 is equal to a magnification of the magnification image formation with the pupil relay lens 133.

Accordingly, when the magnification of the pupil relay lens 133 is greater than 1, the divergence angle 135 of the light beam in the first pupil plane 132 is larger than the divergence angle 136 of the light beam in the objective pupil plane 134. In other words, it is possible to set the divergence angle 136 of the light beam in the objective pupil plane 134 to a smaller angle than the divergence angle 135 of the light beam in the first pupil plane 132.

The illumination light is condensed with the objective lens 102a into a shape elongated in the Y direction on the inspection object substrate 2. The specular reflection light from the inspection object substrate 2 is passed through the objective lens 102a, and is shielded with the TTL illumination mirror 121. In light toward the objective lens 102a, in scattered light occurred from a foreign material or defect on the inspection object substrate 2 or diffraction light occurred by diffraction with a periodical pattern formed on the inspection object substrate 2, the diffraction light occurred with the periodical pattern is shielded with the spatial filter 122 installed on the objective pupil plane 134. On the other hand, the scattered light occurred with the foreign material is not shielded but is transmitted through the spatial filter 122, then is imaged with the imaging lens 105 on the detector 106, and detected as an image signal.

It is desirable that the width of the TTL illumination mirror 121 in the Y direction is sufficient to shield the light beam of the illumination light and the specular reflection light from the inspection object substrate, and narrow not to disturb detection of the scattered light in the vicinity of the specular reflection light in the scattered light generated from the foreign material or defect on the inspection object substrate 2.

The width of the light beam of the illumination light in the Y direction in the position of the TTL illumination mirror 121 is equal to a product between a tangent of the divergence angle of the light beam of the illumination light and a distance from the objective pupil plane 134 to the TTL illumination mirror 121. Accordingly, it is possible to narrow the width of the TTL illumination mirror 121 in the Y direction by reducing the tangent of the divergence angle of the light beam of the illumination light or shortening the distance from the objective pupil plane 134 to the TTL illumination mirror 121. The distance from the objective pupil plane 134 to the TTL illumination mirror 121 is shortened by installing the TTL illumination mirror 121 in as close a position to the objective pupil plane 134 as possible.

On the other hand, the tangent of the divergence angle of the light beam of the illumination light is reduced by, as described above, setting the magnification of the pupil relay lens 133 to a value greater than 1.

That is, as described above, in the configuration of the objective lens 102a having the pupil relay lens 133, the divergence angle 136 in the Y direction of the specular reflection light in the objective pupil plane 134 is smaller in comparison with the divergence angle 135 in the Y direction of the specular reflection light in the first pupil plane 132 when the objective lens 102a is configured only with the condensing lens 131 without the pupil relay lens 133, by setting the magnification of the pupil relay lens 133 to a value greater than 1. As a result, it is possible to reduce the width of the TTL illumination mirror 121 in the Y direction, which is advantageous for high sensitive defect detection.

The vertical detection unit 170a has a pupil detection system 180 including a beam splitter 161, a lens system 162, and a pupil detector 163, and an image plane observation system 190 including a half mirror 164, a lens system 165, and an image plane detector 166. Signals from the pupil detector 163 and the image plane detector 166 are inputted into the overall control unit 301.

The beam splitter 161 is driven with an unshown driving source, and is settable/movable with respect to the optical path. The lens system 162 is configured to form a pupil plane equivalent to the objective pupil plane 134 on the detection surface of the pupil detector 163. The lens system 165 is configured to form an image plane formed with the imaging lens 105 on the detection surface of the image plane detector 166. A CCD sensor and a CMOS sensor and the like are used as the pupil detector 163 and the image plane detector 166 to output a two-dimensional image in a real time manner when image sensing is performed on the inspection object substrate 2 while the stage 152 is continuously moved in one direction. It is possible to obtain a pupil plane image at the same time of acquisition of an image of the surface of the inspection object substrate 2 with the pupil detection system 180 and the image plane observation system 190.

The TTL illumination mirror 121 and the cylindrical lens 116 have an unshown minute angle rotation mechanism about Y axis, for minute adjustment of the position of the beam in the X direction condensed linearly on the inspection object substrate 2. This control mechanism facilitates adjusting the view field positions of the plural detectors 170a, 170b and 170c, the condense position of the illumination light with the oblique illumination unit 112, and the condense position of the TTL illumination light with the TTL illumination unit 111 and the TTL mirror 121 on the inspection object substrate 2, with each other.

The mirror scattered light shielding filter 123 shields a band shaped region elongated in the X direction. The mirror scattered light shielding filter 123 is installed in a position on the objective pupil plane 134 to shield the specular reflection light from the inspection object substrate 2. The spatial filter 122 shields plural band shaped regions elongated in the X direction. The spatial filter 122 is installed in a position to shield a diffraction light pattern formed on the objective pupil plane 134 with the diffraction light occurred from a periodical pattern formed on the inspection object substrate 2.

The spatial filter 122 and the mirror scattered light shielding filter 123 have plates or rods of metal material to shield light with the wavelength of the illumination light. The spatial filter and the mirror scattered light shield filter have a position adjustment mechanism (not shown) to enable adjustment of a light shield position. The mirror scattered light shielding filter 123 and the spatial filter 122 are capable of controlling the shielding width in the Y direction. The control of the shielding width of the mirror scattered light shielding filter 123 and the spatial filter 122 is performed by overlaying plural light shielding filters or replacement with plural light shielding filters having different shielding widths. Note that as the light shielding filter, a liquid crystal filter in which the shape of the light shielding region is controlled with an electric signal, a magneto-optic element, or spatial optical modulator such as a micro mirror array (MEMS) may be used.

It is advantageous in high-sensitivity inspection to change the light shielding width of the mirror scattered light shielding filter 123 in accordance with shape of detected defect. For example, regarding a defect having a low spatial frequency, the scattered light is one-sided in the vicinity of the specular reflection light in the objective pupil plane 134. Accordingly, it is possible to raise the SN ratio of a defect signal by narrowing the light shielding width of the mirror scattered light shielding filter 123.

Further, it is advantageous in high-sensitivity inspection to change the light shielding width of the mirror scattered light shielding filter 123 in accordance with roughness of a background pattern as a noise factor upon inspection or surface roughness of the inspection object substrate 2.

For example, when the roughness (Ra or RMS) is small (e.g., FEOL (Front end of Line) in semiconductor front-end process or transistor process) or the spatial frequency of the roughness is low, as the scattered light occurred with the roughness in the objective pupil plane 134 is concentrated in the vicinity of the specular reflection light, the mirror scattered light shielding filter 123 sufficiently cuts the noise with a narrow light shielding width.

On the other hand, when the roughness is large (e.g., BEOL (Back End of Line) in the semiconductor front-end process or wiring process) or the spatial frequency of the roughness is high, the scattered light of the roughness is spread in a relatively wide range around the specular reflection light in the pupil plane, it is advantageous in the noise reduction to widen the light shielding width of the mirror scattered light shielding filter 123.

Figure 5A:
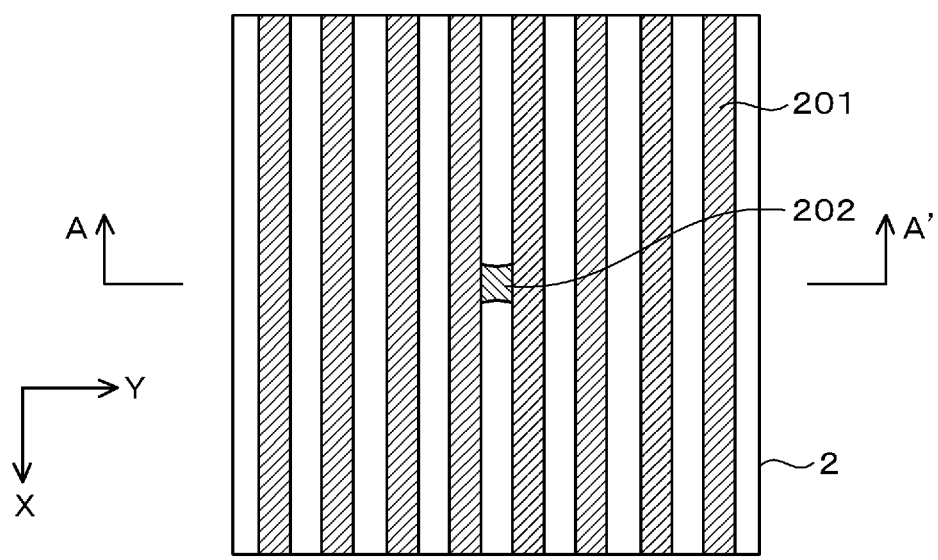
FIG. 5A is a plane diagram of an object substrate to be inspected with the defect inspecting apparatus according to the embodiment of the present invention.
Figure 5B:
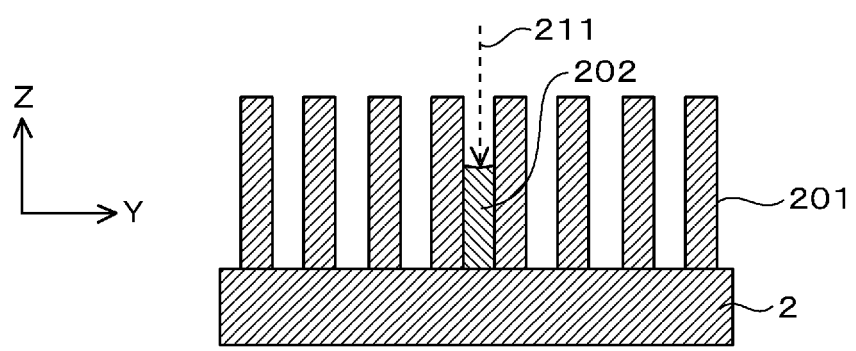
FIG. 5B is an A-A' cross-sectional diagram of the object substrate to be inspected with the defect inspecting apparatus according to the embodiment of the present invention.

FIGS. 5A and 5B show an example of a defect which can be detected with high sensitivity in the present embodiment. FIG. 5A shows a minute bridge defect 202 generated in a line and space (L&S) pattern 201 formed on the inspection object substrate 2. In the figure, the L&S pattern causes short circuit due to the bridge defect 202. In some cases, when the size of the bridge defect 202 is small, short circuit does not completely occur among the wirings. However, such pattern deformation indicates a potential of complete short circuit. Accordingly, in some cases, detection of such pattern deformation as a defect is required.

FIG. 5B shows an A-A' cross section of FIG. 5A. As shown in FIG. 5B, the height of the bridge defect 202 is generally lower than the line and space (L&S) pattern 201. To detect this bridge defect 202, it is necessary to irradiate the illumination light to the inside of the L&S pattern 201. To perform this illumination, it is advantageous to use vertical illumination for illumination from a direction vertical to the substrate (arrow 211).

Further, the polarization upon irradiation of the L&S pattern 201 is advantageous since the linearly polarized light in the Y direction orthogonal to the lengthwise direction of the L&S pattern 201 (X direction in FIG. 5A) is easily transmitted to the inside of the L&S pattern 201. The scattered light occurred from a defect inside the L&S pattern 201 as in the case of the bridge defect 202 is disturbed with the L&S pattern 201 and hardly appears at a shallow angle, but it easily appears in a direction close to the normal line of the inspection object substrate 2. Accordingly, it is advantageous to detect the scattered light in the vicinity of the normal line of the inspection object substrate 2.

That is, upon detection of the bridge defect 202, in the objective pupil plane 134 (the Fourier transformation plane of the objective lens), the scattered light component from the defect is distributed in the vicinity of the specular reflection light reflected in the normal direction from the inspection object substrate 2. Accordingly, it is desirable for high sensitive detection of the bridge defect 202 that in the reflection light incident on the objective lens 102a and reflected in a direction in the vicinity of the normal line from the inspection object substrate 2, the quantity of the scattered light shielded with the TTL illumination mirror 121 provided above the objective lens 102a other than the specular reflection light is reduced, i.e., the scattered light is detected in the vicinity of the specular reflection light as much as possible.

Figure 6A:
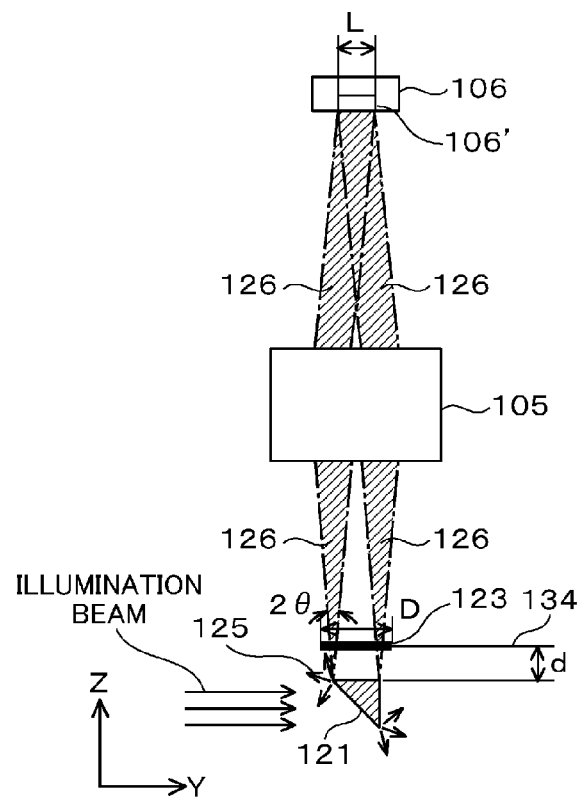
FIG. 6A is a block diagram showing positional relation among a TTL illumination mirror, a mirror scattered light shielding filter, an imaging lens, and a detector in the vertical detection unit of the defect inspecting apparatus according to the embodiment of the present invention.
Figure 6B:
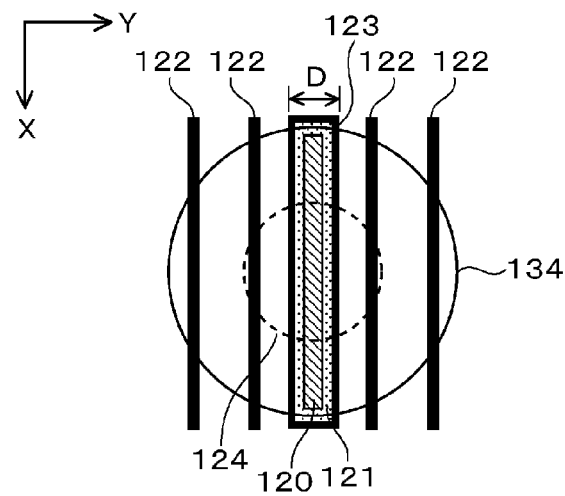
FIG. 6B is a plane diagram of an objective pupil plane of the vertical detection unit of the defect inspecting apparatus according to the embodiment of the present invention viewed from the objective lens side.

FIGS. 6A and 6B show the positional relation among the TTL illumination mirror 121, the spatial filter 122, and the mirror scattered light shielding filter 123 in the vicinity of the objective pupil plane 134. FIG. 6B illustrates the objective pupil plane 134 viewed from the objective lens 102a side. FIG. 6B shows a beam cross section 120 of the specular reflection light upon illumination on the inspection object substrate 2 in the position of the TTL illumination mirror 121. The TTL illumination mirror 121 has a sufficient width to shield the beam. Actually, the illumination light and its specular reflection light is a Gaussian beam having widespread distribution where the intensity is weakened in accordance with distance from the center. Accordingly, it is difficult to completely shield the light even when the width of the TTL illumination mirror 121 is widened.

As an example, to avoid disturbance of detection of the scattered light from a defect (hereinbelow, "defect scattered light"), the width of the TTL illumination mirror 121 is set to a vale from triple to decuple of the width of the beam in the Y direction (the width that the intensity becomes $1/e^2$ with respect to the center). With the configuration using the pupil relay lens 133, it is possible to reduce the width of the beam cross section 120 of the specular reflection light in the position of the TTL illumination mirror 121. Accordingly, it is possible to sufficiently shield the specular reflection light with the TTL illumination mirror 121 having e.g. a width ¼ or smaller than the diameter of the pupil. With this configuration, it is possible to detect a defect with high sensitivity by detecting the scattered light in a region 124 where the defect scattered light is strong in the vicinity of the normal direction of the inspection object substrate.

The spatial filter 122 is used for improvement in defect inspection sensitivity by shielding the diffraction light occurred from a periodical pattern on the inspection object substrate 2. The diffraction light, which occurs in correspondence with wavelength of illumination light irradiated on the inspection object substrate 2 and pattern periodicity is condensed in the objective pupil plane 134 and forms a diffraction pattern. Accordingly, a necessary number of spatial filters in correspondence with pattern of the diffraction light are installed in accordance with a pitch of the diffraction light pattern.

When the illumination beam incident from the TTL illumination unit 111 side or the specular reflection light from the inspection object substrate 2 irradiated with the illumination light reflected from the TTL illumination mirror 121 is irradiated on the surface and the end surface of the TTL illumination mirror 121, scattered light 125 occurs from the surface and end surface of the TTL illumination mirror 121. When the occurred scattered light 125 enters the detector 106, it becomes noise which lowers the defect detection sensitivity. Accordingly, the mirror scattered light shielding filter 123 is used so as to shield the scattered light 125.

The scattered light 125 which becomes noise occurs when the end surface of the TTL illumination mirror 121 receives the illumination light incident from the TTL illumination unit 111 side or the end of the beam (the end of the Gaussian distributed illumination intensity) of the specular reflection light from the inspection object substrate 2. As shown in FIG. 6A, the mirror scattered light shielding filter 123 is installed in the position of the objective pupil plane 134 on the imaging lens 105 side in the vicinity of the TTL illumination mirror 121. Further, as shown in FIG. 6B, a width D of the mirror scattered light shielding filter 123 is set to a value larger than that of the TTL illumination mirror 121 projected on the objective pupil plane 134. With this configuration, it is possible to prevent arrival of the scattered light 125 in the vicinity of the specular reflection light which becomes noise at the imaging lens 105.

In FIG. 6A, in the scattered light 125 occurred from the end surface of the TTL illumination mirror 121, a range of passage of a light beam which arrives at the photoreceptor 106' of the detector 106 is indicated as a region 126 surrounded by an alternate long and short dash line. Assuming that the length of the photoreceptor 106' in the Y direction (lengthwise direction) is L, the image height from a detection optical axis center at the end of the photoreceptor 106' is L/2. Assuming that the focal distance of the imaging lens 105 is f2, the angle of incidence of the light beam 126 on the imaging lens 105 which arrives at image height L/2 is obtained as arcsin(L/(2×f2)). Assuming that this angle is θ, the scattered light emitted from the end of the TTL illumination mirror 121 within an opening angle 2θ may be shielded. Assuming that the distance between the TTL illumination mirror 121 and the mirror scattered light shielding filter 123 is d, it is possible to shield the scattered light emitted from the end of the TTL illumination mirror 121 and arrives at the photoreceptor 106' by setting width D of the mirror scattered light shielding filter 123 to a value thicker than $\Delta=2d\times\tan(\theta)$ with respect to the width of the TTL illumination mirror 121 in the Y direction.

As a particular example, when the width of the TTL illumination mirror 121 in the Y direction is 3 mm, and f2=600 mm, d=5 mm and L=50 mm, 0=2.4° and $\Delta$=0.42 mm hold, and the necessary with D of the mirror scattered light shielding filter 123 is 3.42 mm. In this case, actually the margin of installation position adjustment error is included. Accordingly, the width D of the mirror scattered light shielding filter 123 is wider than 3.42 mm. For example, the width D is 4 mm (adjustment error margin: 0.6 mm) or 5 mm (adjustment error margin: 1.6 mm). To ensure the detection sensitivity while suppress the light shielding ratio of the pupil plane to a low ratio, the amount of the adjustment error margin is a minimum necessary value.

In addition to the above advantages, the mirror scattered light shielding filter 123 has an advantage that when the scattered light, which occurs from a position out of the inspection object in the inspection object substrate 2 and becomes noise, is passed in the vicinity of the illumination specular reflection light, the mirror scattered light shielding filter 123 shields the scattered light to reduce the noise. For example, when the L&S pattern 201 in FIG. 5A has minute roughness or minute pattern deformation not to be necessarily detected as a defect, scattered light which becomes noise occurs. Especially when the period of the spatial frequency of a noise source is long with respect to the illumination wavelength, a noise component easily occurs in the vicinity of the specular reflection light. In such case, it is possible to raise the SN ratio of the defect by widening the light shielding with D of the mirror scattered light shielding filter 123 in the Y direction to a width not to shield a large quantity of the defect scattered light.

Figure 7:
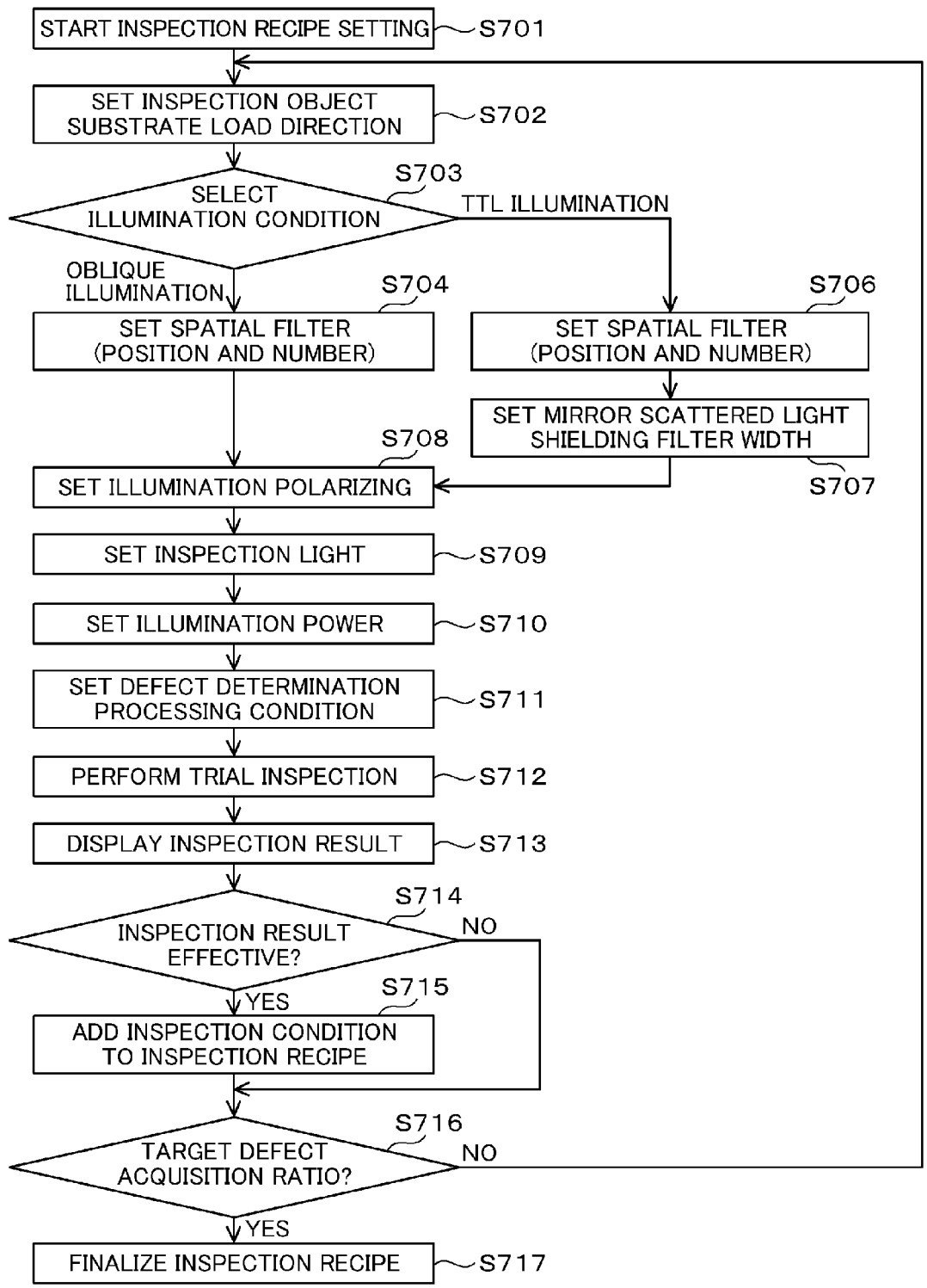
FIG. 7 is a flowchart showing the flow of inspection recipe setting processing in the defect inspecting apparatus according to the embodiment of the present invention.

FIG. 7 is a flowchart of inspection recipe setting. Note that an inspection recipe is an inspection condition (illumination condition, detection condition and defect determination processing condition) or a combination of plural inspection conditions. When inspection is performed under a combination of plural inspection conditions, inspections under the respective inspection conditions are sequentially performed, then the respectively obtained inspection results are integrated to obtain a final inspection result.

In the flow of inspection recipe setting, first, the inspection recipe setting is started (S701), and a load direction of the inspection object substrate 2 is set (S702). The load direction is a direction of setting of the inspection object substrate 2 upon placement of the inspection object substrate 2 on the stage 152. Next, an illumination condition (TTL illumination or oblique illumination) is selected (S703). When the oblique illumination is selected, then setting of the spatial filter 122 regarding the installation position and the number of spatial filters 122 is performed (S704), and the process proceeds to illumination polarizing setting. When the TTL illumination is selected, setting of the spatial filter 122 regarding the installation position and the number of spatial filters to be set is performed (S706). Then the width of the mirror scattered light shielding filter 123 is set (S707), and the process proceeds to illumination polarizing setting (S708). At S708, a wavelength plate 1014 of the TTL illumination unit 111 is adjusted to set the illumination polarizing. Then an inspection light condition of the detector 106 is set (S709). The inspection light condition corresponds to a condition of inspection light direction with the polarizer 104 in the detector 106. Next, the attenuator 1012 and the ND filter 1013 are adjusted to set illumination power (S710).

Then defect determination processing condition is set (S711). With the above processing, one inspection condition is determined.

Here, a trial inspection is performed on the inspection object substrate (S712). The inspection result is displayed on the display unit 302 (S713). The inspection result includes the number of detected defects, whether or not each defect included in a set of defects previously set as inspection object defects has been detected, the acquisition ratio, the number of false detections, the false detection ratio, and the number of defects newly detected based on newly set inspection condition(s) in comparison with the inspection recipe set in the past. The user determines the availability of the inspection condition based on these pieces of information (S714). When the user determines that the inspection condition is available (Yes at S714), the inspection condition is added to the inspection recipe (S715). On the other hand, when the user determines that the inspection condition is not available (No at S714), the process proceeds to S716.

Then it is determined whether or not the number of detections of defects as inspection objects and the detection acquisition ratio become target values with the inspection recipe updated with the above procedure (S716). When these values reach the target values (Yes at S716), the inspection recipe is determined (S717), and the inspection recipe setting ends. When the values do not reach the target values (No at S716), the process returns to S702, to perform the inspection condition setting again.

Figure 8:
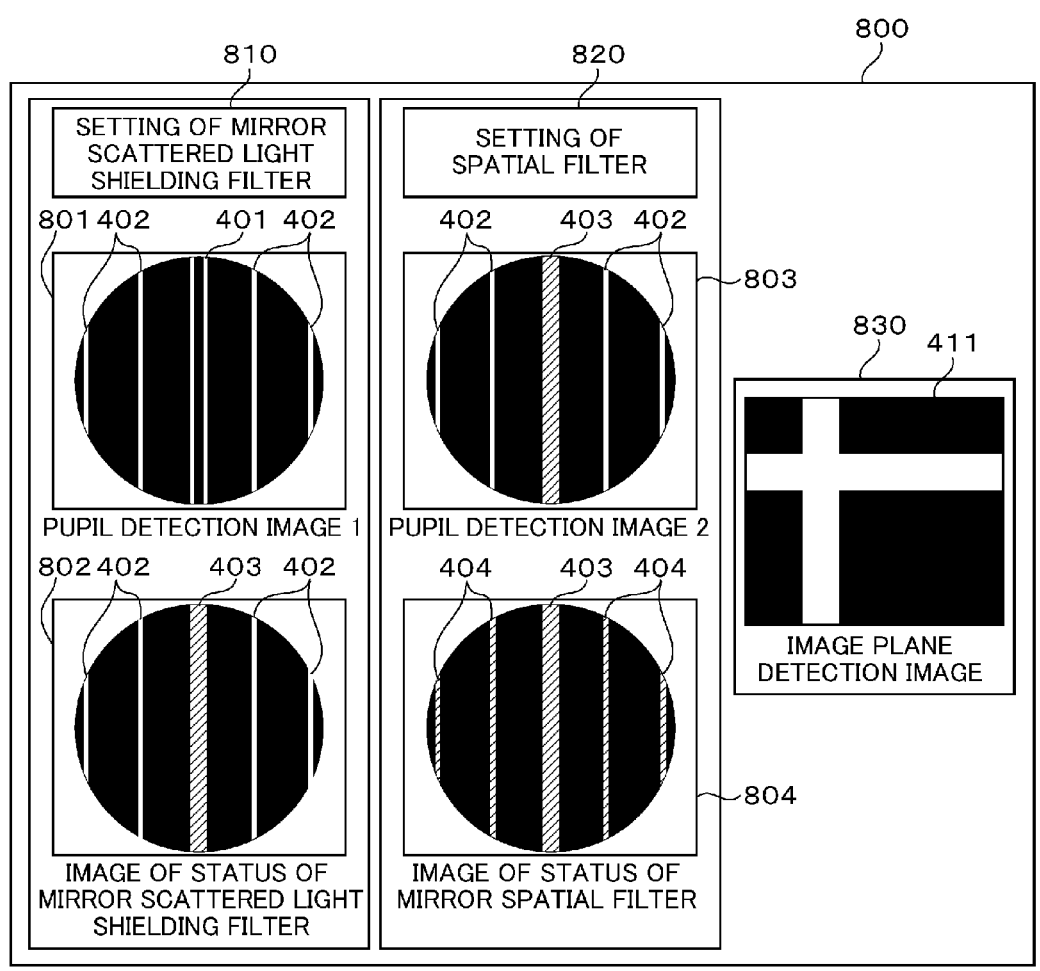
FIG. 8 is a front diagram of a screen displaying a GUI used for setting the mirror scattered light shielding filter and a spatial filter of the defect inspecting apparatus according to the embodiment of the present invention.

FIG. 8 shows an example of a screen 800 of a GUI (Graphic User Interface) used for setting the mirror scattered light shielding filter 123 and the spatial filter 122 (S704, S706 and S707 in FIG. 7). Note that in the image example in FIG. 8, the vertical direction corresponds to the X direction in the objective pupil plane 134, and the horizontal direction, the Y direction in the objective pupil plane 134, shown in FIG. 4B. The screen 800 of the GUI has an image display region 810 to indicate the setting status of the mirror scattered light shield filter, an image display region 820 to indicate a spatial filter setting status, and a region 830 to indicate an image plane detection image.

A pupil detection image 1:801, displayed in the image display region 810 showing a setting status of the mirror scattered light shield filter, shows light intensity distribution of a pupil plane detected with the pupil detector 163 of the pupil detection system 180. FIG. 8 shows an example of a shadow of the TTL illumination mirror 121 shielding the specular reflection light (a region between two white lines at the center of a TTL illumination mirror image 401:a pupil detection image 1:801) and intensity distribution of diffraction light in the objective pupil plane 134 (on-pupil diffraction light image 402) with a repetitive pattern formed on the inspection object substrate 2. In the pupil detection image 1:801, the TTL illumination mirror image 401 appears as a specular reflection light image and a shadow overlapped with the image of a scattered component in the vicinity of the image.

On the other hand, an image of the status of the mirror scattered light shielding filter 123 (position and width of the light shielding region) is displayed in a mirror scattered light shield filter status image 802. As the pupil detection image 1:801, an image in a status before installation of the mirror scattered light shielding filter 123 is stored in the storage unit 304, and the display is fixed on the image. As the mirror scattered light shield filter status image 802, the light intensity distribution of the objective pupil plane 134 in a status where the mirror scattered light shielding filter 123 is installed is displayed in a real time manner. With the installation and adjustment of the mirror scattered light shielding filter 123, a light shielding region 403 is displayed as a dark region (in FIG. 8, a region hatched with white lines). It is possible to set the position and the light shielding width of the light shielding region of the mirror scattered light shielding filter 123 so as to accurately shield specular reflection light and scattered light which becomes noise in the vicinity of the specular reflection light by simultaneously displaying the pupil detection image 1:801 and the mirror scattered light shield filter status image 802.

As a pupil detection image 2:803 displayed in the image display region 820 indicating the spatial filter setting status, a light intensity distribution image of the pupil plane in the status where the mirror scattered light shielding filter 123 is installed is displayed. The image is stored in the storage unit 304, and the display is fixed. It is possible to clearly observe pattern diffraction light without bright saturation of a region in the vicinity of the specular reflection light using a pupil detector having a dynamic range (about 50 to 60 dB) approximately the same as that of a general CCD camera, by adjusting the storage time, sensitivity or display gain of the pupil detector 163 in correspondence with diffraction light in the status where the mirror scattered light shielding filter 123 is installed.

As a spatial filter status image 804 displayed in the image display region 820 indicating the spatial filter setting status, the light intensity distribution of the objective pupil plane 134 in the status where the mirror scattered light shielding filter 123 and the spatial filter 122 are installed is displayed in a real time manner, and the light shielding regions of the mirror scattered light shielding filter 123 and spatial filter 122 are displayed as dark regions (in FIG. 8, regions hatched with white lines). It is possible to set a light shielding region 404 of the spatial filter so as to accurately shield the pattern diffraction light by simultaneously display the pupil detection image 2:803 and the spatial filter status image 804.

The example of sequentially adjusting the mirror scattered light shielding filter 123 and the spatial filter 122 is as described above. Further, it may be configured such that the mirror scattered light shielding filter 123 and the spatial filter 122 are simultaneously or alternately adjusted while the sensitivity is arbitrarily adjusted in the real time display of the pupil detection image.

An image plane image 411 outputted from the image plane detector 166, displayed in the image plane detection image display region 830, is also simultaneously displayed together with the pupil detection images displayed in the image display region 810 to indicate the setting status of the mirror scattered light shielding filter and the image display region 820 to indicate the spatial filter setting status. With this configuration, it is possible to adjust the mirror scattered light shielding filter 123 and the spatial filter 122 on the objective pupil plane 134 while check the image plane image 411 as a real time image of the image plane.

First Modification

Figure 9:
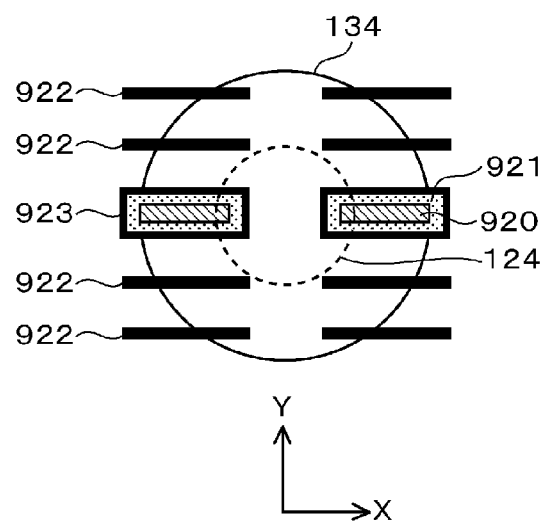
FIG. 9 is a plane diagram of the objective pupil plane for dipole illumination of the defect inspecting apparatus according to a first modification of the present invention viewed from the objective lens side.

FIG. 9 shows a schematic diagram in the vicinity of the pupil plane of an optical system to perform dipole illumination via an objective lens as a first modification of the embodiment. The constituent elements not shown in the figure are basically the same as those described in the embodiment. In the present modification, in the TTL illumination unit 111, using a diffraction optical element (DOE) or a combination of lens system and a light shielding element, a beam having distribution where a center of a linear beam is omitted, is formed. In this manner, illumination with two separate condensed beams will be referred to as "dipole illumination" here. It is possible to raise the detection efficiency of scattered light in the region 124 in the normal direction of the inspection object substrate in which the defect scattered light is strong, and it is possible to detect a defect with higher sensitivity, by using a TTL illumination mirror 921 and a mirror scattered light shielding filter 923, in which the two separate beams are incident on the objective lens 102a, and the light passes through the central part of the pupil plane.

Further, as the dipole illumination is adopted, a spatial filter 922 also has a structure where the central portion is omitted as in the case of the mirror scattered light shielding filter 923. Further, regarding illumination condensation in the X direction, a low spatial frequency illumination light component around the objective lens disappears, and the relative density of a high spatial frequency illumination light component around the outer periphery of the objective lens is relatively high. Accordingly, as the condensation width of the liner illumination in the X direction formed on the inspection object substrate 2 is shortened, and the spatial resolution is raised, it is possible to improve the detection sensitivity for minute defects.

Note that it is not necessary to form a beam having distribution where a central portion of liner beam is omitted in the TTL illumination unit 111. The dipole illumination may be realized by irradiating a general linear beam to a TTL illumination mirror 921 where a central portion is omitted. In this case, as the end of the TTL illumination mirror 921 receives a high intensity part of the illumination beam and strong noise scattered light occurs, the installation of the mirror scattered light shielding filter 923 is necessary. Further, it is advantageous that the width of the mirror scattered light shielding filter 923 is wider than that described in the embodiment.

Second Modification

Figure 10:
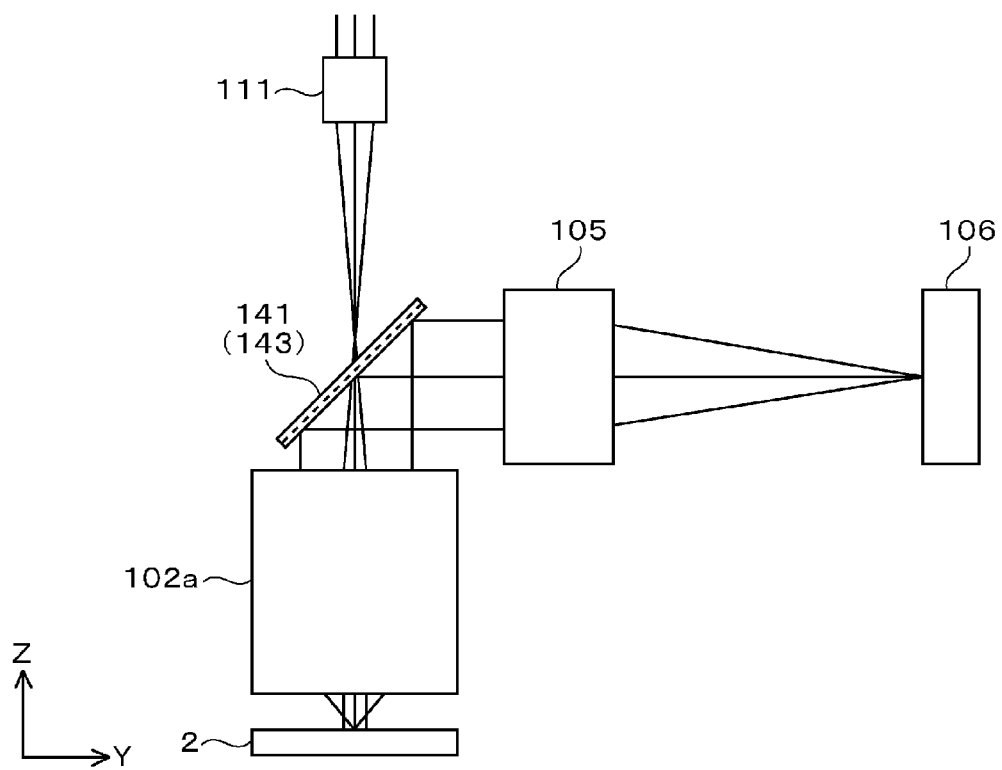
FIG. 10 is a block diagram showing a schematic configuration of the detection unit using a mirror with slit in the defect inspecting apparatus according to a second modification of the present invention.

As a second modification of the embodiment, FIG. 10 shows a block diagram of a vertical detection unit of an optical system using a mirror with slit 141 in the objective pupil plane 134. The linear illumination beam formed with the TTL illumination unit 111 is passed through a slit-shaped opening of the mirror with slit 141, and linearly condensed via the objective lens 102a on the inspection object substrate 2. The scattered light and the reflection light including the defect scattered light occurred on the inspection object substrate 2 is condensed with the objective lens 102a. Then the light is reflected with the mirror with slit 141 except the specular reflection light component of the illumination light. Then the light is condensed with the imaging lens 105, and detected with the detector 106. The other constituent elements are the same as those described in the embodiment, accordingly, the explanations of those elements will be omitted.

FIGS. 11A and 11B show schematic diagrams of the mirror with slit 141.

As shown in FIG. 11A, a slit-shaped thin opening 142 is formed at the central portion, and the illumination light emitted from the TTL illumination unit 111 is passed through. The illumination light passed through the opening 142 is transmitted through the objective lens 102a and irradiated to the inspection object substrate 2. In the scattered light occurred on the inspection object substrate 2 irradiated with the illumination light, scattered light transmitted through the objective lens 102a is incident on the mirror with slit 141. The scattered light received with the mirror with slit 141 except the slit 142 is reflected to the imaging lens 105 side, and image is formed on the detection surface 106' of the detector 106. On the other hand, in the scattered light occurred on the inspection object substrate 2, scattered light including specular reflection light from the inspection object substrate 2 entered the slit 142 of the mirror with slit 141 does not reach the detector 106 through the slit 142.

FIG. 11B shows an example using a mirror with slit 143 corresponding to the dipole illumination according to the first modification. The defect scattered light arrived at the central portion of the mirror with slit 143 is reflected with the mirror with slit 143 and detected. The TTL illumination mirror 121 described in the embodiment reflects the illumination light with a slim bar shaped reflection mirror. On the other hand, in the configuration using the mirror with slit 143 according to the present modification, the illumination light is passed through the slit. Accordingly, it is advantageously possible to accurately form the illumination light distribution on the sample without degradation of accuracy of condensation of the illumination light due to distortion of mirror shape. Further, the mirrors with slit 141 and 143 have a structure where a long thin opening 142 or 144 is provided in a flat mirror, and it is possible to easily maintain the surface accuracy. Accordingly, the detection image is not degraded with the reflection.

Note that the present invention is not limited to the embodiment but various modifications are included. For example, the embodiment has been described in detail for clearly explaining the present invention. The invention is not necessarily limited to an embodiment having all the described constituent elements. Further, a part of the constituent elements of an embodiment may be replaced with those of another embodiment. Further, the constituent element(s) of an embodiment may be added to those of another embodiment. Further, addition, deletion and/or replacement may be made with respect to a part of the constituent elements of an embodiment with other constituent elements.

Further, the shown control lines and information lines are those considered necessary for the sake of explanation, but all the control lines and information lines as a product are not necessarily shown. Actually, it may be considered that almost all the constituent elements are mutually connected.

The invention may be embodied in other specific forms without departing from the spirit or essential characteristics thereof. The present embodiment is therefore to be considered in all respects as illustrative and not restrictive, the scope of the invention being indicated by the appended claims, rather than by the foregoing description, and all changes which come within the meaning and range of equivalency of the claims are therefore intended to be embraced therein.

What is claimed is:

1. A defect inspecting apparatus comprising:
    a table for placing a sample, capable of moving within a plane;
    a light source that emits laser;
    an optical path branching mirror that branches an optical path of the laser emitted from the light source;
    an oblique illuminator that condenses the laser, proceeded in one of optical paths branched with the optical path branching mirror, into a line shape, and irradiates the laser to the sample placed on the table unit from an oblique direction;
    a condenser that condenses the laser, proceeded in another one of optical paths branched with the optical path branching mirror, into a line shape;
    a mirror that reflects the laser, condensed in a line shape with the condenser, to deflect the optical path of the laser;
    an objective lens that receives the laser, with the optical path deflected with the mirror, then irradiates the laser to the sample placed on the table from a vertical direction, and condenses reflected scattered light from the sample irradiated with the laser;
    a spatial filter that shields diffraction light, occurred from a periodical pattern formed on the sample, in the reflected scattered light from the sample, condensed with the objective lens, and shields the scattered light occurred from the mirror;
    an imaging lens that receives the reflected scattered light from the sample, not shielded with the spatial filter, and forms an image of the reflected scattered light;
    a detector that detects the image of the reflected scattered light formed with the imaging lens; and
    a signal processor that processes a detection signal obtained by detecting the image of the reflected scattered light with the detector, to detect a defect on the sample,
    wherein the objective lens has a condensing lens and a pupil relay lens that re-forms a first pupil, formed with the condensing lens, to form a second pupil.

2. The defect inspecting apparatus according to claim 1, wherein the spatial filter has: a light shield that shields the diffraction light occurred from the periodical pattern formed on the sample; and a light shield that shields the scattered light occurred in the mirror with the laser incident on the mirror and the specular reflection light from the sample, and
    wherein the light shield that shields the scattered light has a width larger than a width of the mirror projected on a pupil plane.

3. The defect inspecting apparatus according to claim 1, wherein the mirror unit and the spatial filter unit are provided on a second pupil plane of the objective lens unit or in the vicinity of the second pupil plane.

4. The defect inspecting apparatus according to claim 1, further comprising:
    a pupil detection system for observation of the second pupil plane formed with the pupil relay lens; and
    an image plane observation system for observation of the image of the reflected scattered light formed with the imaging lens.

5. The defect inspecting apparatus according to claim 1, further comprising an oblique detection optical system that condenses and detects light, reflected and scattered in an oblique direction with respect to the sample, in the reflected scattered light occurred from the sample by illumination in the oblique direction with the oblique illuminator or illumination from a vertical direction via the objective lens with the laser, with the optical path deflected with the mirror.

6. A defect inspecting method comprising:
    condensing laser emitted from a light source in a line shape;
    reflecting the laser, condensed in the line shape, with a mirror;
    irradiating the reflected laser via an objective lens to a sample placed on a table from a vertical direction;
    condensing reflected scattered light from the sample, irradiated with the laser from the vertical direction, with the objective lens;
    shielding diffraction light occurred from a periodical pattern formed on the sample, in the reflected scattered light from the sample, condensed with the objective lens, and scattered light occurred from the mirror, with a spatial filter;

receiving the reflected scattered light from the sample, not shielded with the spatial filter, with an imaging lens, and forming an image of the reflected scattered light;

detecting the formed image of the reflected scattered light with a detector; and processing a detection signal obtained by detecting the image of the reflected scattered light with the detector and detecting a defect on the sample, wherein the reflected scattered light from the sample is condensed with a condensing lens of the objective lens and forming an image on a first pupil plane, and wherein an image of the reflected scattered light from the sample formed on the first pupil plane is formed on a second pupil plane with a pupil relay lens.

7. The defect inspecting method according to claim 6, wherein the spatial filter shields the scattered light occurred with the mirror from the laser incident on the mirror and the specular reflection light from the sample, as scattered light occurred from the mirror, with a light shielding unit having a width larger than a width of the mirror unit projected on a pupil plane.

8. The defect inspecting method according to claim 6, wherein the mirror and the spatial filter are provided on the second pupil plane of the objective lens unit or in the vicinity of the second pupil plane.

9. The defect inspecting method according to claim 6, further comprising:

observing the second pupil plane formed with the pupil relay lens with a pupil detection system; and observing the image of the reflected scattered light formed with the imaging lens with an image plane observation system.

10. The defect inspecting method according to claim 6, further comprising a step of branching laser emitted from the light source, condensing the branched laser in a line shape and irradiating the laser to the sample placed on the table from an oblique direction, and detecting reflected scattered light occurred from the sample from the laser irradiated from the oblique direction, with an oblique detection system provided in a direction inclined with respect to a surface of the sample.

* * * * *